(12) United States Patent
Svidenko et al.

(10) Patent No.: US 7,844,101 B2
(45) Date of Patent: Nov. 30, 2010

(54) SYSTEM AND METHOD FOR PERFORMING POST-PLATING MORPHOLOGICAL CU GRAIN BOUNDARY ANALYSIS

(75) Inventors: Vicky Svidenko, Sunnyvale, CA (US); Lior Levin, Raanana (IL)

(73) Assignee: Applied Materials Israel, Ltd., Rehovot (IL)

(*) Notice: Subject to any disclaimer, the term of this patent is extended or adjusted under 35 U.S.C. 154(b) by 1004 days.

(21) Appl. No.: 11/343,792

(22) Filed: Jan. 31, 2006

(65) Prior Publication Data

US 2006/0274931 A1    Dec. 7, 2006

Related U.S. Application Data

(60) Provisional application No. 60/648,871, filed on Jan. 31, 2005.

(51) Int. Cl.
*G06K 9/00* (2006.01)
*G06K 9/40* (2006.01)

(52) U.S. Cl. .................. 382/145; 382/110; 382/266
(58) Field of Classification Search ............. 382/100, 382/141, 144, 145, 276, 286, 266, 110, 199; 348/86; 438/14, 618, 652
See application file for complete search history.

(56) References Cited

U.S. PATENT DOCUMENTS

| 5,376,409 | A  | * | 12/1994 | Kaloyeros et al. | 427/248.1 |
| 6,339,020 | B1 | * | 1/2002  | Weihs et al.     | 438/643   |
| 6,458,694 | B2 | * | 10/2002 | Ogure et al.     | 438/652   |
| 2002/0037641 | A1 | * | 3/2002 | Ritzdorf et al. | 438/618   |

OTHER PUBLICATIONS

Svidenko et al., "Powerful Quantitative Monitoring Tool Improves CU and W Plug Fill", Nanochip Technology Journal, Issue Two, 2004, pp. 5-11.

* cited by examiner

*Primary Examiner*—Yon Couso
(74) *Attorney, Agent, or Firm*—SNR Denton US LLP (57) ABSTRACT

Grain size variations within a copper film are quantified by analyzing an SEM image of a portion of the copper film, determining an approximate total length of grain boundaries within the SEM image, and calculating a grain boundary density based on the approximate total length of the grain boundaries and the area of the copper film represented in the SEM image. The calculated grain boundary density allows for correlating plating and anneal process parameters, as well as electrical and reliability performance.

20 Claims, 9 Drawing Sheets

SYSTEM AND METHOD FOR PERFORMING POST-PLATING MORPHOLOGICAL CU GRAIN BOUNDARY ANALYSIS

RELATED APPLICATIONS

The present application is a NONPROVISIONAL of and claims priority to U.S. Provisional Patent application No. 60/648,871, filed Jan. 31, 2005, incorporated herein by reference.

FIELD OF THE INVENTION

The present invention relates generally to a system and method for performing copper film grain size characterization during semiconductor fabrication and development, and more particularly to a system and method for determining the copper grain boundary density.

BACKGROUND

In semiconductor fabrication, "missing metal" defects, electromigration, and stress migration are issues that often occur after chemical-mechanical polishing. The effects and severity of the issues strongly depend on the post-electrochemical plating (ECP) copper film grain size, orientation, and intrinsic stress in patterned structures. Deformed and highly stressed crystals are transformed into unstressed crystals by recovery, recrystallization and grain growth. During the recrystallization process, the sheet resistance (Rs) typically drops 20 to 30%, attaining a sheet resistance approaching that of pure, bulk copper. Copper grain size, orientation, film stress, and sheet resistance also continuously change after the ECP process due to stabilization of vacancies, dislocations, and other crystalline imperfections and impurities. The final copper film characteristics also depend critically on the plating process, bath chemistry, and anneal process conditions.

To determine potential electrical and reliability problems, it is therefore useful to analyze the microstructure characteristics of the copper film. Typically, copper film grain size characterization efforts have been performed using electron back scatter diffraction (EBSD), transmission electron microscopy (TEM) imaging, or by focused ion beam (FB) imaging. Usually 1000 grains per sample are traced manually, the tracing is digitized, and the grain areas are measured by image analysis software. The measured areas are then converted to an equivalent grain diameter. Such measurement techniques, however, need to be performed off-line, are time-consuming, and significantly limit fast process characterization, making copper grain boundary monitoring impractical. In addition, further analysis of the grain size distribution involves consideration of at least two parameters (average and variance), thus complicating the characterization.

Accordingly, there is a need for a system and method for performing in-line and efficient grain size characterization that overcomes the above problems.

SUMMARY OF THE INVENTION

In one embodiment, the present invention provides systems and methods for quantifying feature-level, die-to-die, and wafer-to-wafer copper (Cu) grain size variations during semiconductor fabrication or development. These systems and methods provide an efficient utility for ECP process development and monitoring on both blanket and device wafers, and correlate measurements obtained during such processes to plating and anneal process parameters, as well as to electrical and reliability performance.

In particular, the present invention is directed to a system for analyzing grain characteristics of a copper film plated on a wafer. The system includes a grain boundary quantification processor configured to analyze a first image of a portion of the copper film, determine an approximate total length of grain boundaries within the first image, and calculate a first grain boundary density based on the approximate total length of the grain boundaries and an area of the first image.

The system may further include a scanning electron microscope (SEM) for obtaining the first image, and a focused ion beam for sputtering at least the portion of the wafer. The focused ion beam is preferably configured to slightly mill grains of different orientation at different rate and to remove a portion of an oxidation layer formed on the copper film in order to enhance the edge contrast of copper grains on the wafer.

In another aspect, the present invention is also directed to method for analyzing copper grain characteristics of a copper film plated on a wafer. This method provides for determining the approximate total length of grain boundaries within a first image of a portion of the copper film, and calculating the grain boundary density based on the approximate total length of the grain boundaries and an area of the first image.

BRIEF DESCRIPTION OF THE DRAWINGS

The present invention is illustrated by way of example, and not limitation, in the figures of the accompanying drawings, in which.

DETAILED DESCRIPTION

Described herein are systems and methods for performing post-plating morphological grain boundary analyses on metal films, especially copper films, plated on semiconductor wafers or other substrates. It should be remembered, however, that the embodiments described herein are intended to be examples only. That is, the scope of the present invention is not intended to be limited to the embodiments described herein, and instead should be measured only in terms of the claims following this description of the present invention.

Figure 1:
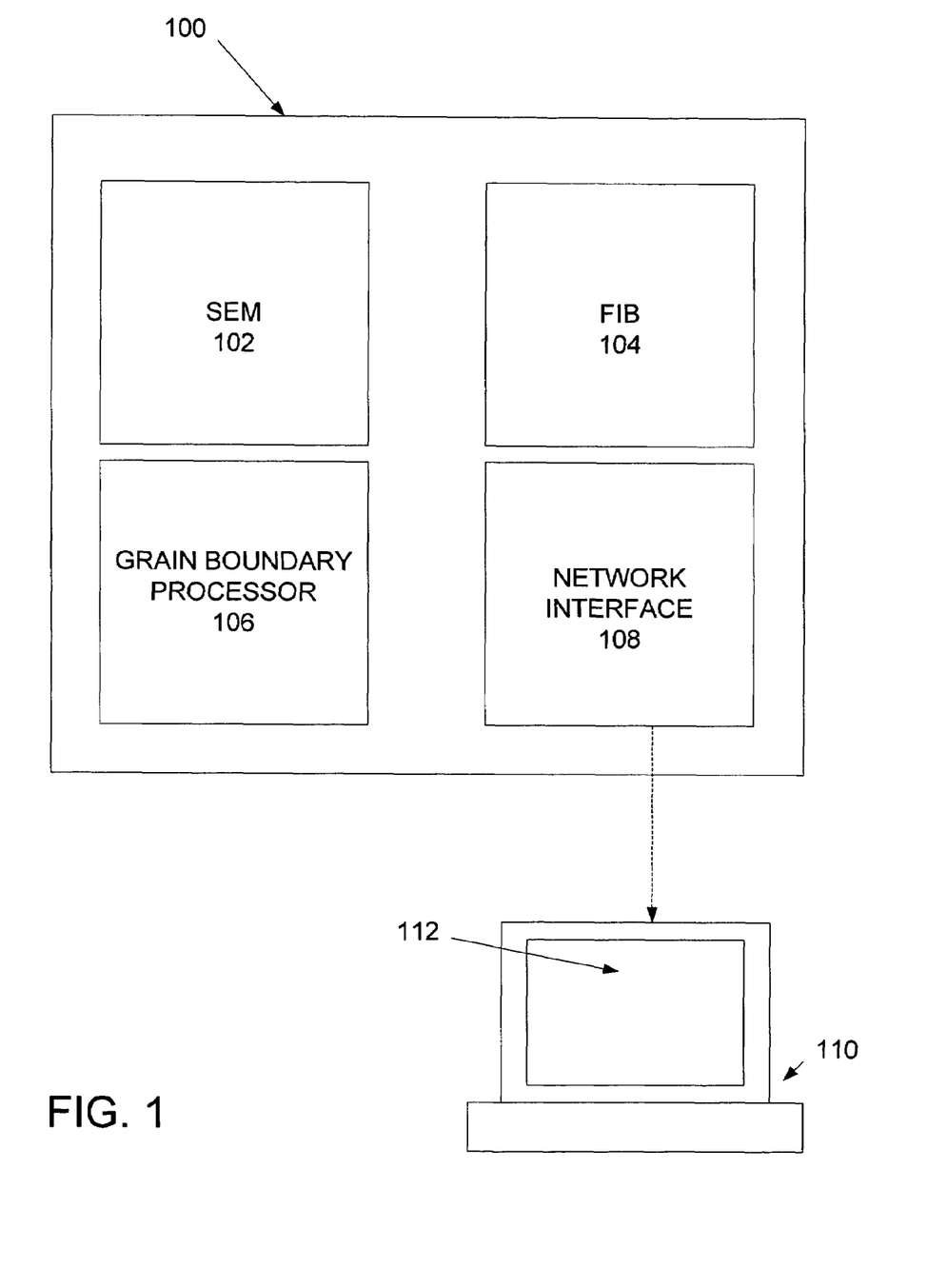
FIG. 1 illustrates an example of an instrument for performing copper grain boundary analysis according to an embodiment of the present invention.

Referring first to FIG. 1, an analysis instrument 100 configured according to an embodiment of the present invention is shown. This analysis instrument may include a scanning electron microscope (SEM) 102, a focused ion beam (FIB) tool 104 and a grain boundary quantification processor 106. In one embodiment, described in detail below, the grain boundary quantification processor is configured to determine a density of grain boundaries of a metal (e.g., copper) film plated over a semiconductor wafer or other substrate. This is accomplished, in part, by analyzing one or more images of the metal film as produced by the SEM 102 to determine an approximate total length of grain boundaries within an area of the metal film represented by the image. To aid in determining this length of the grain boundaries, the metal film may be subject to processing by the FIB tool 104 so as to remove any oxides that may be present on the film and to use the fact that grains of different orientation are milled at different rate and thereby enhance edge contrast of the grain boundaries for imaging.

The SEM 102 is a microscope that uses a finely focused electron beam scanned across a sample to produce high resolution images. The FIB 104 uses a finely focused beam of gallium (Ga+) ions. This focused beam of gallium ions is rastered on the surface of the material to be analyzed. As the ion beam strikes the surface of the film, a small amount of material is sputtered, or dislodged, from that surface. As indicated above, this technique may be used to remove oxide layers from the metal film and polish the metal grains. As scanning electron microscopes and focused ion beams are well-known in the art, detailed specifics of their construction are not included herein.

The grain boundary quantification processor 106 performs the analysis of a wafer, or a portion of the wafer, to determine a grain boundary (GB) density. As discussed in further detail below, the grain boundary quantification processor 106 measures the total Cu grain boundary length within an SEM image and calculates the total grain boundary length per area, also referred to herein as the GB density. The value of the GB density may then be used to analyze plating and anneal process parameters, as well as electrical and reliability performance.

The analysis instrument 100 may also include a network interface 108 for exporting results obtained by the GB processor 106 to an external display device for engineering analysis. In the exemplary embodiment shown in FIG. 1, the results may be exported to a computer or workstation 110 having a display 112. The computer may be connected to the network interface 108 via a local area network, a wide area network, a wireless connection, or any other known data transferring means. Alternatively, rather than sending the results to an external display, the analysis instrument 100 may also include an integrated display (not shown) so that the results obtained by the grain boundary quantification processor can be viewed directly on the analysis instrument.

Figure 2:
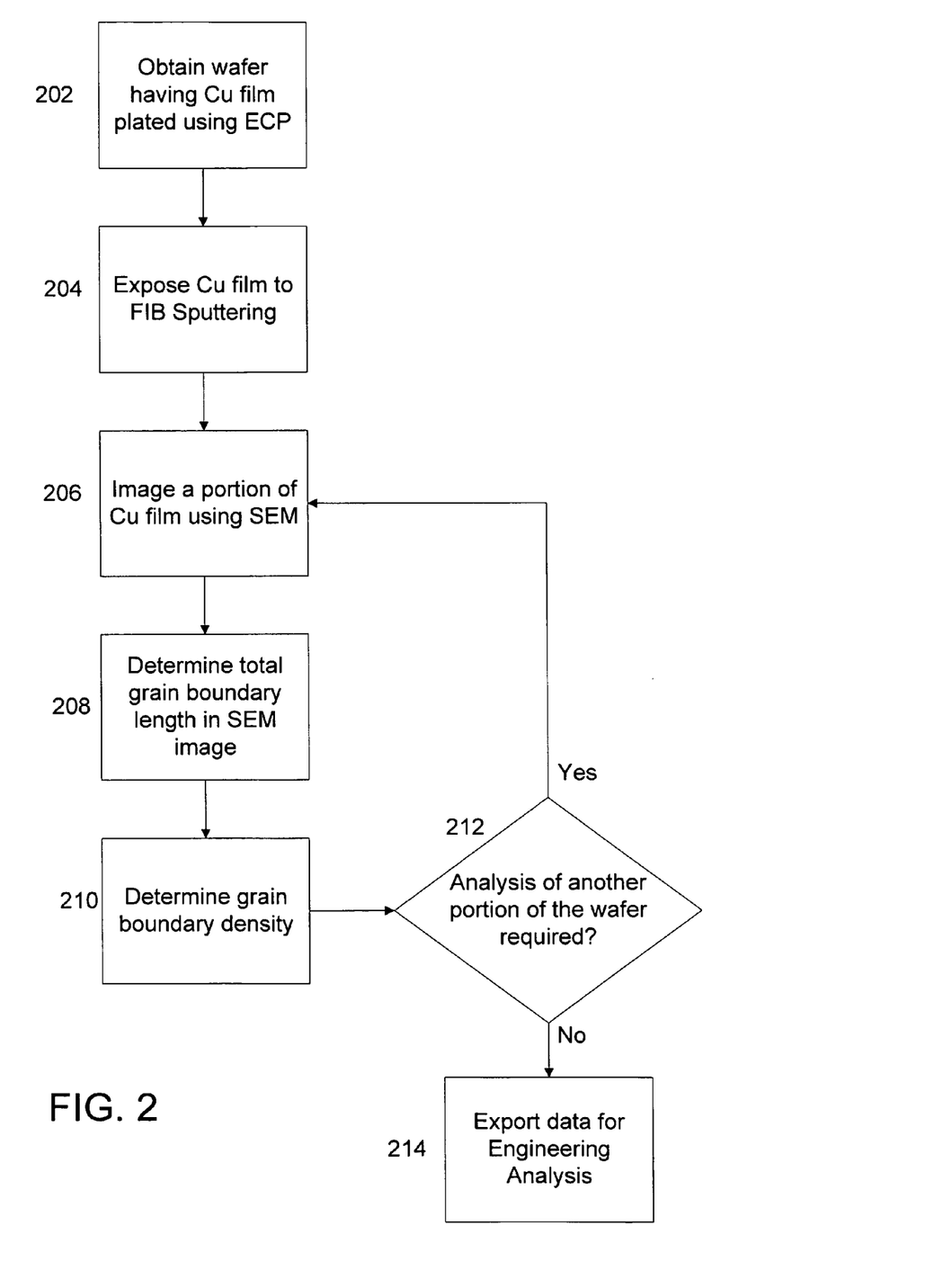
FIG. 2 is a flow diagram illustrating a process for performing copper grain boundary analysis according to an embodiment of the present invention.

FIG. 2 is a flow chart illustrating a process for performing Cu grain boundary analysis using the apparatus in FIG. 1. First, in step 202, a wafer having a plated copper film is obtained. The wafer may or may not be polished by chemical mechanical polishing process (CMP). In step 204, at least the portion of the copper plating to be analyzed is exposed to FIB sputtering. In step 206, an SEM image of a portion of the wafer is then taken. The field of view of the SEM image can be chosen based on the needs of the user and the type of Cu patterns to be tested. For example, the field of view for an image may be approximately 5 µm to 10 µm if an individual pattern or feature on the wafer is to be analyzed. The SEM may also be used to image the entire wafer.

Figure 3:
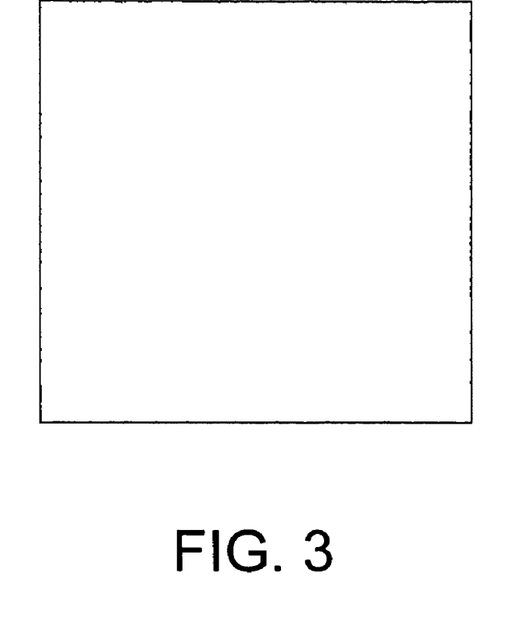
FIG. 3 is an exemplary SEM image of a plated copper film before FIB sputtering.
Figure 4:
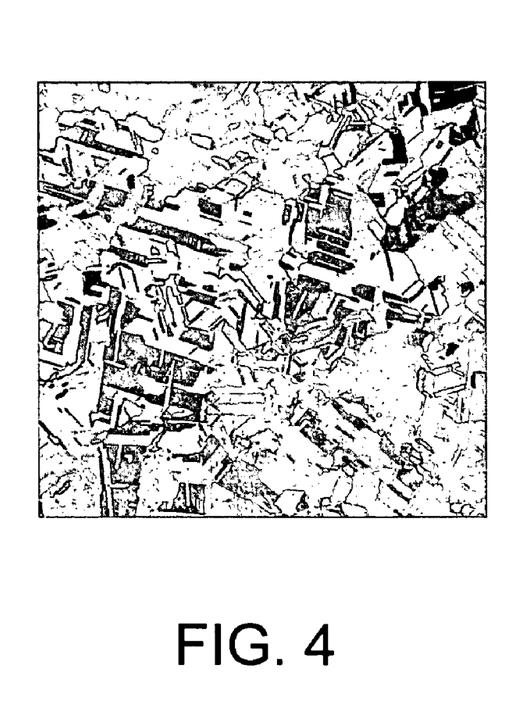
FIG. 4 is an exemplary SEM image of a plated copper film after FIB sputtering.
Figure 5:
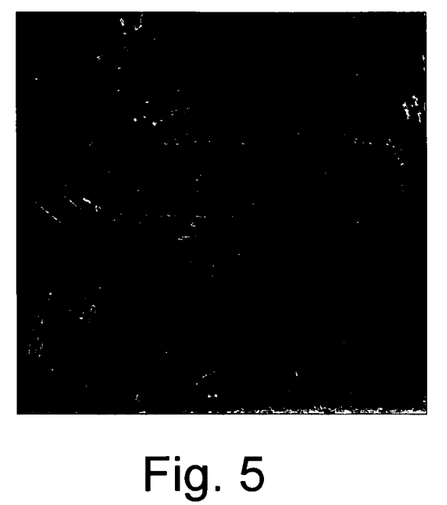
FIG. 5 is an exemplary SEM image of a plated and polished Cu film before FIB sputtering.
Figure 6:
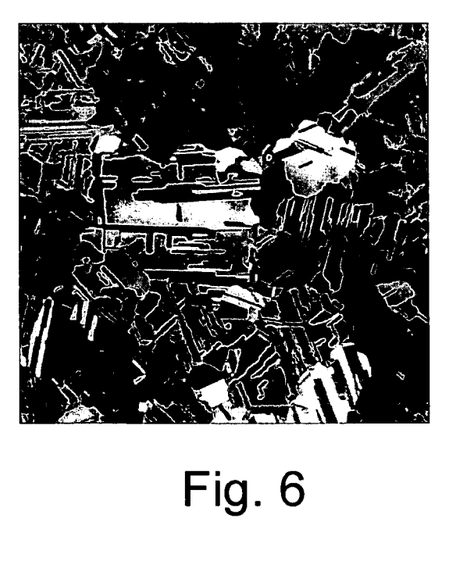
FIG. 6 is an exemplary SEM image of a plated and polished Cu film after FIB sputtering.

The purpose of performing FIB sputtering prior to SEM imaging is to sufficiently expose the Cu grain boundaries for analysis. Copper grains on a typical post-ECP wafer are indistinct and therefore difficult to analyze and quantify (an exemplary SEM image of a plated Cu film before FIB sputtering is shown in FIG. 3). Therefore, in order to better distinguish the Cu grain boundaries, the Cu surface to be tested is exposed to FIB sputtering. Short exposure of the Cu surface to a focused ion beam removes the top layer of oxidation from the CU plating and causes grains of different orientation to be milled at different rates, thereby enhancing the edge contrast of the grains. As a result, an SEM image of the Cu film after FIB sputtering shows distinct Cu grain boundaries, which can then be readily analyzed by the Cu grain boundary quantification processor (an exemplary SEM image of a plated Cu film after FIB sputtering is shown in FIG. 4). Copper surfaces post CMP are already polished and the grains are partially visible under SEM. (an exemplary SEM image of a plated and polished Cu film before FIB sputtering is shown in FIG. 5) However, an oxidation layer quickly formatting on the copper surface significantly limits grains visibility. Sputtering the area of interest with ions removes the oxide and exposes the grains, thus enabling their clear visibility in SEM processor (an exemplary SEM image of a plated and polished Cu film after FIB sputtering is shown in FIG. 6)

Also, in order to sufficiently expose the grain boundaries, it is preferable that the SEM 102 and the FIB 104 are provided within a single instrument so that an SEM image may be taken after FIB sputtering without removing the sample from the instrument. This prevents contact of the sample with oxygen, which could potentially cause reformation of the oxidation layer previously removed during FIB sputtering.

In step 208, the total grain boundary length of the sample within the SEM image field of view is determined. To determine the total grain boundary length, a grain boundary analysis is first performed to identify the presence and location of each grain boundary within the SEM image. Image processing techniques for performing a grain boundary analysis, for example the Canny edge detector algorithm, are well-known in the art, and the present invention is not intended to be limited to any one specific method or technique. Once the grain boundary analysis is performed, the total length of all the grain boundaries within the analyzed field is then measured. The total length may be measured in terms of pixels, micrometers, or any other unit of measurement.

Figure 7:
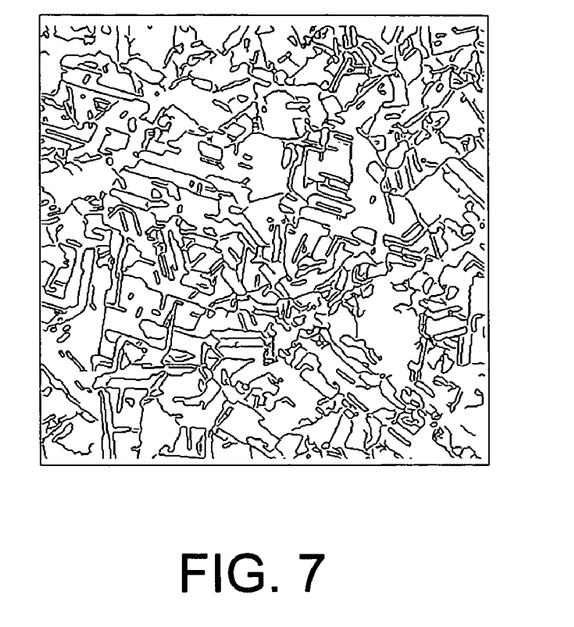
FIG. 7 illustrates an example of results of a grain boundary analysis performed on the SEM image of FIG. 4 in accordance with an embodiment of the present invention.

FIG. 7 shows the results of an exemplary grain boundary analysis of the SEM image in FIG. 4. As seen in FIG. 7, the grain boundary analysis shows a detailed outline of each grain boundary in the SEM image, permitting an accurate measurement of the total length of the grain boundary.

Returning to FIG. 2, the GB density is then calculated in step 210. As discussed above, the GB density is calculated by dividing the total grain boundary length by the total area of copper in the SEM image. Generally, the larger the average grain size, the shorter the GB length in the inspected image, corresponding to a lower Cu GB density. Thus, there is an inverse-proportion trend between a measured GB density and grain size.

In step 212, it is determined whether analysis of the GB density is required for any other portion of the wafer. If further analysis is required, the process returns to step 206 and an SEM image is taken of the next portion of the wafer. By determining the GB density of numerous portions of the wafer, copper film reliability can be quantified for each tested portion, allowing for more precise monitoring of the wafer's performance.

If no more analysis is required, the final data may then be exported for engineering analysis (step 214). Of course, the data may alternatively be exported in real time after analysis of each portion of the wafer. To simplify inspection of the data, the system may classify each image based on its result and export the classification result to a defect database library, which can be maintained and stored either in a memory internal to the analysis instrument or in an external database.

Figure 8:
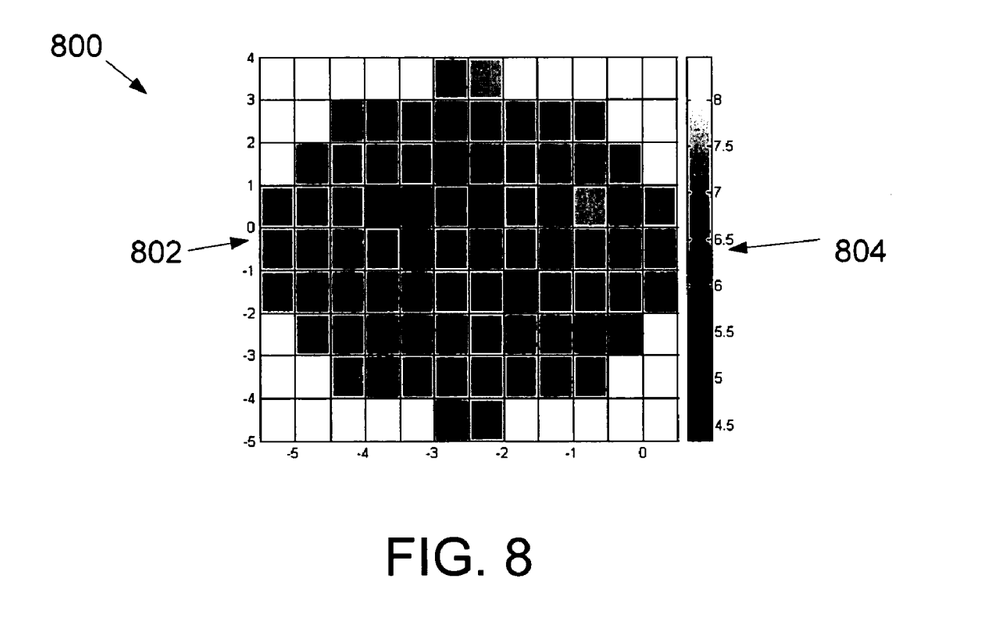
FIG. 8 illustrates an example of a grain boundary distribution map according to an embodiment of the present invention.

A grain boundary density distribution map may also be created to provide a graphical display of the data for each wafer. FIG. 8 shows one example of a grain boundary distribution map 800. In this example, the grain boundary distribution map includes a grid 802 having twelve horizontal squares and twelve vertical squares. Each square in the grid corresponds to a portion of a wafer, and preferably represents one die on the wafer. Alongside the grid 802 is a scale 804 indicating various gradations of color or shades of gray. In the embodiment shown in FIG. 8, the scale 804 is configured to indicate a specific color or grey-scale shade for each GB density between approximately 4.5 and 8.5. Each square representing a die may then filled in with the color or shade corresponding to a GB density measured for a location within that die. Accordingly, the grain boundary distribution map provides a graphical illustration of the GB density for various portions of the wafer simultaneously, making analysis of the wafer simpler and quicker. Of course, although one example of a grain boundary distribution map has been shown, it should be understood that the map can be presented in various configurations or designs. The grid in the map may also include more or less squares, depending on the design of the wafer.

Thus, the present invention provides a simple, robust, automated, and reliable in-line technique for GB density characterization. As discussed below, it has been found that GB density exhibits a high correlation with the Cu film sheet resistance over a wide range of grain sizes, as well as critical dimensions of device structures. As a result, the GB density calculation may be used for analysis and monitoring of potential reliability and electrical performance issues. As also illustrated below, quantification of the GB density additionally enables monitoring of the cross-wafer uniformity of ECP process and anneal parameters due to the correlation between the GB density and the ECP parameters.

Experiment 1: Correlation of GB Density to ECP and Post-ECP Process Parameters

Fifteen wafers were prepared by ECP pulse plating using the SlimCell™ ECP from Applied Materials, Inc. ECP pulse plating and post-ECP anneal conditions were varied to generate a wide range of Cu film grain sizes. In particular, variations in grain sizes and copper film sheet resistances were achieved with pulsed plating at frequencies ranging from 10 Hz to 1000 Hz. Post-ECP in situ anneal processing was investigated within a 90° C. to 300° C. temperature range, with anneal duration times ranging from 10 sec to 1 hr.

Figure 9:
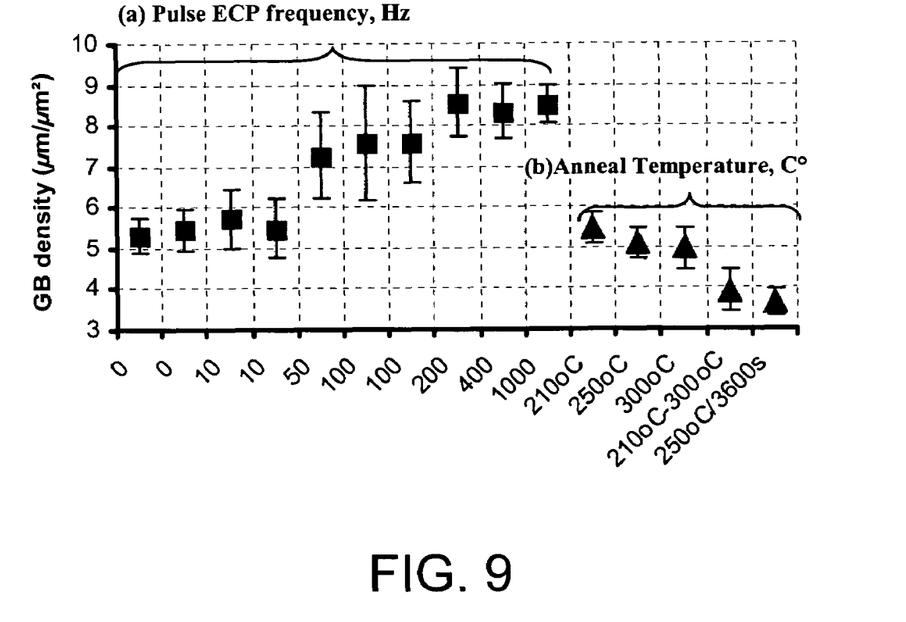
FIG. 9 is a chart showing correlations between grain boundary density and ECP pulse plating and post-ECP anneal parameters.

GB density of the blanket wafers was then measured using the system and process described above. As shown in FIG. 9, the GB density parameters resulting from the various ECP pulse plating and post-ECP anneal conditions ranged from 3.5 to 8.5 $\mu m/\mu m^2$. The data illustrated numerous correlation between GB density and the ECP and post-ECP conditions. In particular, the data illustrated that the GB density increases (i.e., grain size decreases) with increasing pulse frequency, leveling off to a minimum grain size at 200 Hz and above. The GB density decreases with increasing anneal thermal budget, tracking the expected increase in grain size. The GB density decreased with increasing anneal temperature. Anneal processes also decreased the GB density significantly. As shown in FIG. 9, the lowest GB density was achieved with a 1 hour anneal at 250° C.

Experiment 2: Correlation of GB Density to Four Point Probe Sheet Resistance

The sheet resistance (Rs) of each of the wafers prepared in Experiment 1 was measured with a four point probe technique. Sheet resistance (Rs) is the electrical resistance of a thin sheet of a material with uniform thickness as measured across opposite sides of a unit square pattern, and is often used to analyze the speed and reliability of patterned copper films.

Figure 10:
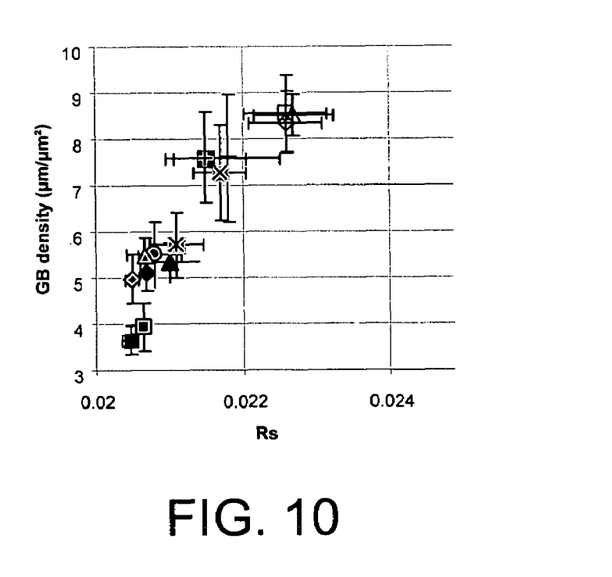
FIG. 10 is a chart showing correlations between grain boundary density and sheet resistance.

The GB density was then plotted versus the sheet resistance for each wafer, as illustrated in FIG. 10. As can be seen from FIG. 10, there is a strong correlation between the GB density parameter and the four point probe sheet resistance, Rs, over the full range of grain sizes modulated by plating and anneal process variations. In particular, as the GB density increases, the Rs also increases, since GB density is the main contributor to the resistivity. Grain boundaries slow the electrons flow trough the interconnect lines, thus reducing the conductivity.

Experiment 3: Correlation of GB Density to Patterned Structure Sizes

Figure 11:
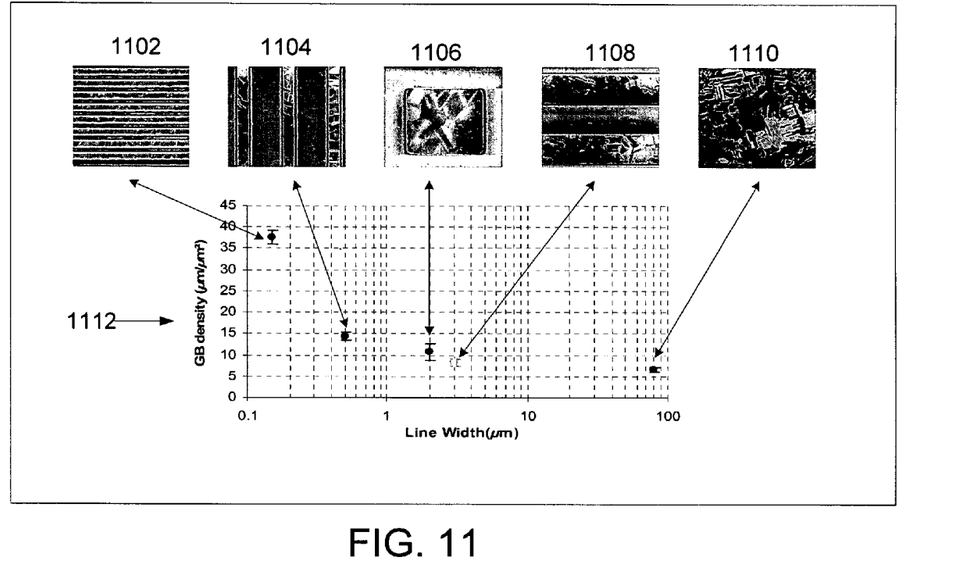
FIG. 11 is a chart showing correlations between grain boundary density and patterned feature size.

Re-crystallization of Cu over a trench topography on patterned test structures was examined to determine the correlation between GB density and patterned structure sizes. GB density was measured on the following feature sizes as shown in FIG. 11: dense lines with 150 nm lines and spaces (1102), narrow sparse lines with 500 nm lines and 1800 nm spaces (1104), small square pads of 2000 nm each side (1106), and wide 3 μm lines with 3 μm spaces (1108). All data on the patterned structures was compared with data on large 80 μm square pads (1110). The large pad results were considered equivalent to those on blanket wafers, because their dimensions were much larger than the average grain size (approximately 1 to 2 μm).

Each feature type was sampled in 7 different locations on each wafer. For each type of feature, an optimal field of view (FOV) was chosen to maximize GB visibility. The GB density was then normalized to the area of metal and the FOV to allow sampling-independent comparison for different line widths. This was performed using the following calculation:

$$GBdensity = \frac{\frac{GBlength[pixels]}{480[pixels]} \cdot FOV[\mu m]}{\frac{ROIarea[pixels]}{(480 \times 480)[pixels]} \cdot FOV^2[\mu m^2]}$$

$$= \frac{GBlength \cdot 480}{ROIarea \cdot FOV} \left[\frac{\mu m}{\mu m^2}\right]$$

where GBlength is the grain boundary length measured in pixels, FOV is the field of view, ROIarea is the area of the region of interest, and the image size was 480 pixels by 480 pixels.

FIG. 11 shows a graph demonstrating the trend seen between grain size and patterned feature size. Particularly, the GB density increases significantly (grain size decreases) as the feature line width decreases. For large features, GB density saturates at the blanket wafer film value for line widths greater than approximately 3 μm.

Figure 12:
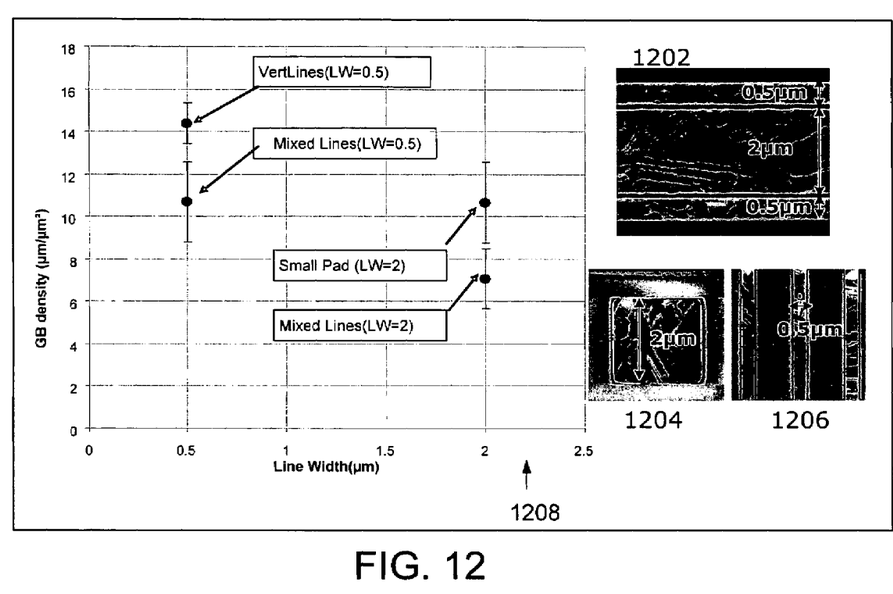
FIG. 12 is another chart showing correlations between grain boundary density and patterned feature size.

Referring now to FIG. 12, the GB density was then analyzed for small square pads of 2000 nm on each side (1202), mixed lines of 500 nm and 2 μm (1204), and narrow sparse lines with 500 nm lines and 1800 nm spaces (1206) in order to compare the GB density of densely spaced structures. As seen in graph 1208, on densely spaced structures the GB density is smaller than the trend line from isolated features would indicate. This is a result of the grains being linked within densely spaced features due to nucleation in the overburden. The grain structure growth propagates across densely spaced features. Thus, very tightly spaced trenches do not behave independently from a grain growth perspective, but rather, may behave as a single line with a larger effective line width.

Figure 13:
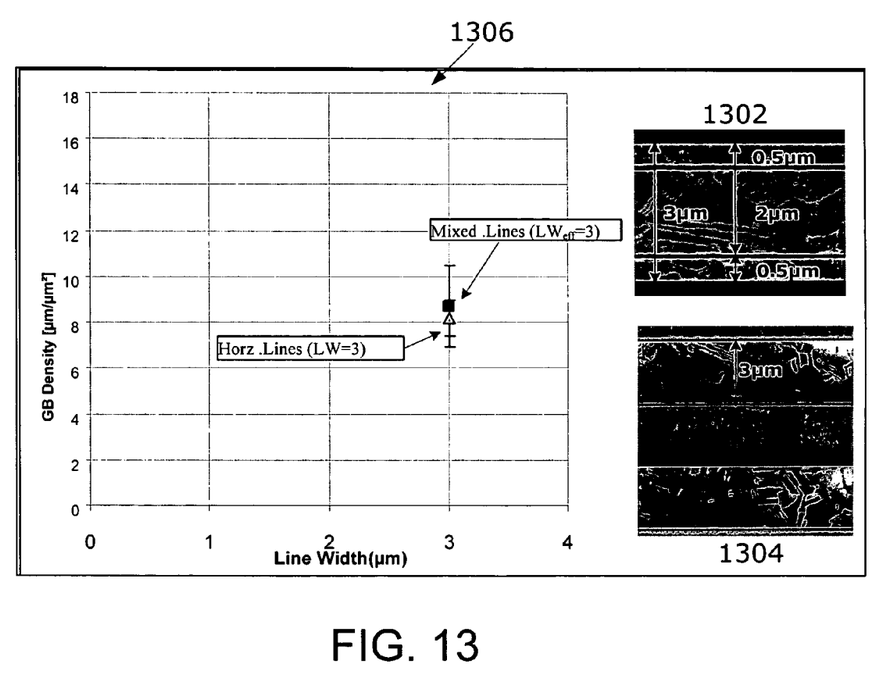
FIG. 13 is yet another chart showing correlations between grain boundary density and patterned feature size.

This is further illustrated in FIG. 13, which illustrates results of a comparison of the GB density for mixed lines of 500 nm and 2 μm (1302) with 3 μm lines with 3 μm spaces (1304). As can be seen from graph 1106, treating the coupled lines as one line of larger effective line width yields a GB density close to the value for a single monolithic line of the same line width.

Thus, systems and methods for performing post-plating morphological grain boundary analyses on metal films, especially copper films, plated on semiconductor wafers or other substrates have been described. It will be apparent to those of ordinary skill in the art that many more implementations than those described herein are possible and that such variations are within the scope of this invention. Accordingly, the invention is not to be restricted except in light of the following claims and their equivalent.

What is claimed is:

1. A system for analyzing grain characteristics of a copper film plated on a wafer comprising a grain boundary quantification processor configured to analyze a first image of a portion of the copper film, determine an approximate total length of grain boundaries within the first image, and calculate a first grain boundary density based on the approximate total length of the grain boundaries and an area of the film represented in the first image.

2. The system of claim 1 further including a scanning electron microscope for obtaining the first image.

3. The system of claim 1 further including a focused ion beam for sputtering at least the portion of the wafer in order to enhance edge contrast of copper grains on the wafer.

4. The system of claim 1 wherein the focused ion beam is configured to remove a portion of an oxidation layer formed on the copper film.

5. The system of claim 1 wherein the scanning electron microscope and the focused ion beam are provided in a single housing such that the first image can be obtained by the scanning electron microscope following sputtering by the focused ion beam without exposing the wafer to oxygen.

6. The system of claim 1 wherein the scanning electron microscope is configured to obtain a second image of a different portion of the wafer, the second image having a predetermined area; and wherein the grain boundary quantification processor is configured to determine an approximate total length of grain boundaries within the second image and calculates a second grain boundary density based on the approximate total length of the grain boundaries and the area of the second image.

7. The system of claim 1 further including a network interface for exporting results produced by the grain boundary quantification processor to an external display device.

8. The system of claim 1 further including means for displaying results produced by the grain boundary quantification processor.

9. The system of claim 1 further including means for displaying a grain boundary density distribution map graphically illustrating results from the grain boundary quantification processor of at least two separate portions of the wafer.

10. A method for analyzing copper grain characteristics of a copper film plated on a wafer, comprising:
    determining an approximate total length of grain boundaries within a first image of a portion of the copper film using a grain boundary processor;
    calculating grain boundary density within the copper film based on the approximate total length of the grain boundaries and an area of the copper film represented by the first image using the grain boundary processor.

11. The method of claim 10 further including obtaining the first image of the portion of the copper film using a scanning electron microscope.

12. The method of claim 11 further including sputtering with a focused ion beam, by the scanning electron microscope, at least the portion of the copper film in order to enhance edge contrast of copper grains prior to obtaining the first image.

13. The method of claim 10 wherein determining the approximate total length of grain boundaries includes performing, by the grain boundary processor, a grain boundary analysis to identify locations of the grain boundaries within the first image, and measuring a length of each identified grain boundary using the grain boundary processor.

14. The method of claim 11 further including obtaining a second image of a different portion of the copper film using the scanning electron microscope.

15. The method of claim 14 further including:
    determining an approximate total length of grain boundaries within the second image using the grain boundary processor; and
    calculating grain boundary density based on the approximate total length of the grain boundaries in the second image and an area of the film represented in the second image using the grain boundary processor.

16. The method of claim 15 further including displaying a grain boundary density distribution map graphically illustrating grain boundary densities of at least two separate portions of the film on a display.

17. A system for analyzing grain characteristics of a copper film plated on a wafer comprising:
    means for determining an approximate total length of grain boundaries within a first image of a portion of the copper film;
    means for calculating grain boundary density of the copper film based on the approximate total length of the grain boundaries and an area of the film represented within the first image.

18. The system of claim 17 further including means for obtaining the first image of the portion of the copper film using a scanning electron microscope.

19. The system of claim 18 further including means for sputtering at least the portion of the copper film with a focused ion beam in order to enhance the edge contrast of copper grains prior to obtaining the first image.

20. The system of claim 19 wherein the means for determining the approximate total length of grain boundaries includes means for performing a grain boundary analysis to identify locations of grain boundaries with the first image, and means for measuring a length of each identified grain boundary.

* * * * *